United States Patent [19]
Kaetsu et al.

[11] Patent Number: 5,152,758
[45] Date of Patent: Oct. 6, 1992

[54] ELECTRORESPONSIVE HYDROGEL AND PHYSIOLOGICALLY ACTIVE SUBSTANCE RELEASE CONTROL SYSTEM

[75] Inventors: Isao Kaetsu, Takatsuki; Yasushi Morita; Akira Ohtori, both of Toyonaka, all of Japan

[73] Assignee: Senju Pharmaceutical Co., Ltd., Osaka, Japan

[21] Appl. No.: 556,332

[22] Filed: Jul. 23, 1990

[30] Foreign Application Priority Data

Aug. 4, 1989 [JP] Japan .................. 1-203629

[51] Int. Cl.$^5$ .............................................. A61K 9/22
[52] U.S. Cl. ...................... 604/890.1; 604/20; 604/65
[58] Field of Search .......... 604/20, 50, 65-67, 604/246, 890.1, 891.1, 892.1; 128/DIG. 12, 639, 632

[56] References Cited

U.S. PATENT DOCUMENTS

| | | | |
|---|---|---|---|
| 3,618,601 | 11/1971 | Richardson | 604/20 |
| 3,837,339 | 9/1974 | Aisenberg et al. | 604/20 |
| 4,003,379 | 1/1977 | Ellinwood, Jr. | 604/891.1 |
| 4,020,830 | 5/1977 | Johnson et al. | 128/632 |
| 4,181,128 | 1/1980 | Swartz | 604/20 |
| 4,383,529 | 5/1983 | Webster | 604/20 |
| 4,401,722 | 8/1983 | Clark, Jr. | 128/632 |
| 4,494,950 | 1/1985 | Fischell | |
| 4,538,616 | 9/1985 | Rogoff | 604/66 |
| 4,596,575 | 6/1986 | Rosenberg et al. | 604/891.1 |
| 4,639,244 | 1/1987 | Rizk et al. | 604/891.1 |
| 4,685,463 | 8/1987 | Williams | 604/50 |
| 4,705,503 | 11/1987 | Dorman et al. | 604/20 |
| 4,718,430 | 1/1988 | Holzer | 128/632 |
| 4,822,337 | 4/1989 | Newhouse et al. | 604/50 |

FOREIGN PATENT DOCUMENTS 0245535 11/1987 European Pat. Off.

OTHER PUBLICATIONS

Tanaka et al., Science, vol. 218, Oct. 29, 1982, pp. 467-469.
Han et al., Chem. Abstr., vol. 109, No. 15, (1988), p. 329, Abstract No. 1251885.
Nakamoto et al., Chem. Abstr., vol. 108, No. 11, (1988), pp. 344, Abstract No. 91137n.

Primary Examiner—C. Fred Rosenbaum
Assistant Examiner—Mark Bockelman
Attorney, Agent, or Firm—Wenderoth, Lind & Ponack

[57] ABSTRACT

An electroresponsive hydrogel produced by alkali hydrolysis of a copolymer comprising N-isopropylacrylamide, an ionic monomer and a crosslinking agent; and a physiologically active substance release control system comprising a biosensor, an amplifier and an electroresponsive hydrogel containing physiologically active substance are disclosed. The hydrogel of the present invention is capable of releasing a physiologically active substance alone in an amount corresponding to the applied voltage with excellent reproducibility by contracting and reswelling in good response to the loading and unloading of an external stimulation voltage, it can be advantageously used in a physiologically active substance release control system capable of releasing an essential physiologically active substance in a necessary amount according to changes in physiological conditions. Also, the physiologically active substance release control system of the present invention using this hydrogel is useful for the treatment of various diseases including diabetes mellitus.

9 Claims, 5 Drawing Sheets

ELECTRORESPONSIVE HYDROGEL AND PHYSIOLOGICALLY ACTIVE SUBSTANCE RELEASE CONTROL SYSTEM

BACKGROUND OF THE INVENTION

The present invention relates to release control of a physiologically active substance, more specifically to an electroresponsive hydrogel and a physiologically active substance release control system comprising a biosensor (particularly a biosensor comprising an enzyme-immobilized ion sensitive field effect transistor), an amplifier and an electroresponsive hydrogel containing a physiologically active substance.

For example, in the treatment of diabetes mellitus, it is considered desirable to release insulin into blood according to blood sugar level for maintenance of the level in a particular range, irrespective of food intake time and food consumption. In general, a mode for physiologically active substance administration capable of releasing an essential physiologically active component in a necessary amount according to changes in physiological conditions in vivo (hereinafter referred to as "physiologically active substance release control system") is useful for the treatment of various diseases.

As insulin pumps, there have been developed, for example, portable infusion pumps such as the MILL-HILL injector (Harvard Apparatus) and implantable administration systems such as the sophisticated, telemetry-modulated implantable infusion pump (John Hopkins University). However, these insulin pumps allow continuous release of a given amount of insulin at a constant rate, and cannot release an essential physiologically active substance in a necessary amount according to changes in physiological conditions in vivo.

Also, there are many reports on biosensors that convert chemical information in vivo to electric signals, but studies of carriers suitable to the controlled storage and release of the desired physiologically active substance should be made for the realization of release control of a physiologically active substance by means of these biosensors.

With a potential for use in these applications, hydrogel, which shows expansion-contraction changes in response to external stimulation such as light, temperature, pH or electric field, has recently drawn much attention. For example, drug release could be reportedly controlled using a temperature-sensitive gel [You Han Bae et al.: Makromol. Chem. Rapid Commun., 8, 481 (1987)]. Also, Tanaka et al. [Science, 218, 467 (1982)] reported an electroresponsive hydrogel for the first time.

However, any configuration of release control system characterized by its temperature-based drug release control is considered as of little practical value because it is difficult to control the system due to temperature control, etc. when used in human bodies, etc. In addition, it remains unknown what is an optimal configuration for practical use of an electroresponsive hydrogel. With this background, there are demands for development of a release control system which can serve for practical use and a hydrogel which can serve as a component thereof.

SUMMARY OF THE INVENTION

It is an object of the present invention to provide a system capable of releasing an essential physiologically active substance in a necessary amount according to changes in physiological conditions in vivo.

It is another object of the present invention to provide a hydrogel usable in such a system, i.e., a hydrogel capable of releasing or retaining an physiologically active substance in response to appropriate external stimulation.

With the aim of accomplishing these objects, the present inventors made intensive investigations and found that an electroresponsive hydrogel prepared with a given composition by a given process serves well for these objects, thus completing a configuration of said hydrogel. Then, the present inventors succeeded in configuring a release control system capable of controlling release of a physiologically active substance from hydrogel according to the concentration of an indicator chemical substance in vivo by combining said electroresponsive hydrogel with a particular biosensor and an voltage amplifier, which resulted in completion of the invention.

Accordingly, the present invention comprises:

1) A physiologically active substance release control system wherein an electroresponsive hydrogel containing a physiologically active substance is contracted according to the concentration of an indicator chemical substance in vivo to cause it to release the physiologically active substance, by amplifying a voltage generated from a biosensor by means of an amplifier and introducing it into the electroresponsive hydrogel.

2) An electroresponsive hydrogel produced by alkali hydrolysis of a copolymer comprising N-isopropylacrylamide, an ionic monomer and a crosslinking agent.

DETAILED DESCRIPTION OF THE INVENTION

Figure 1:
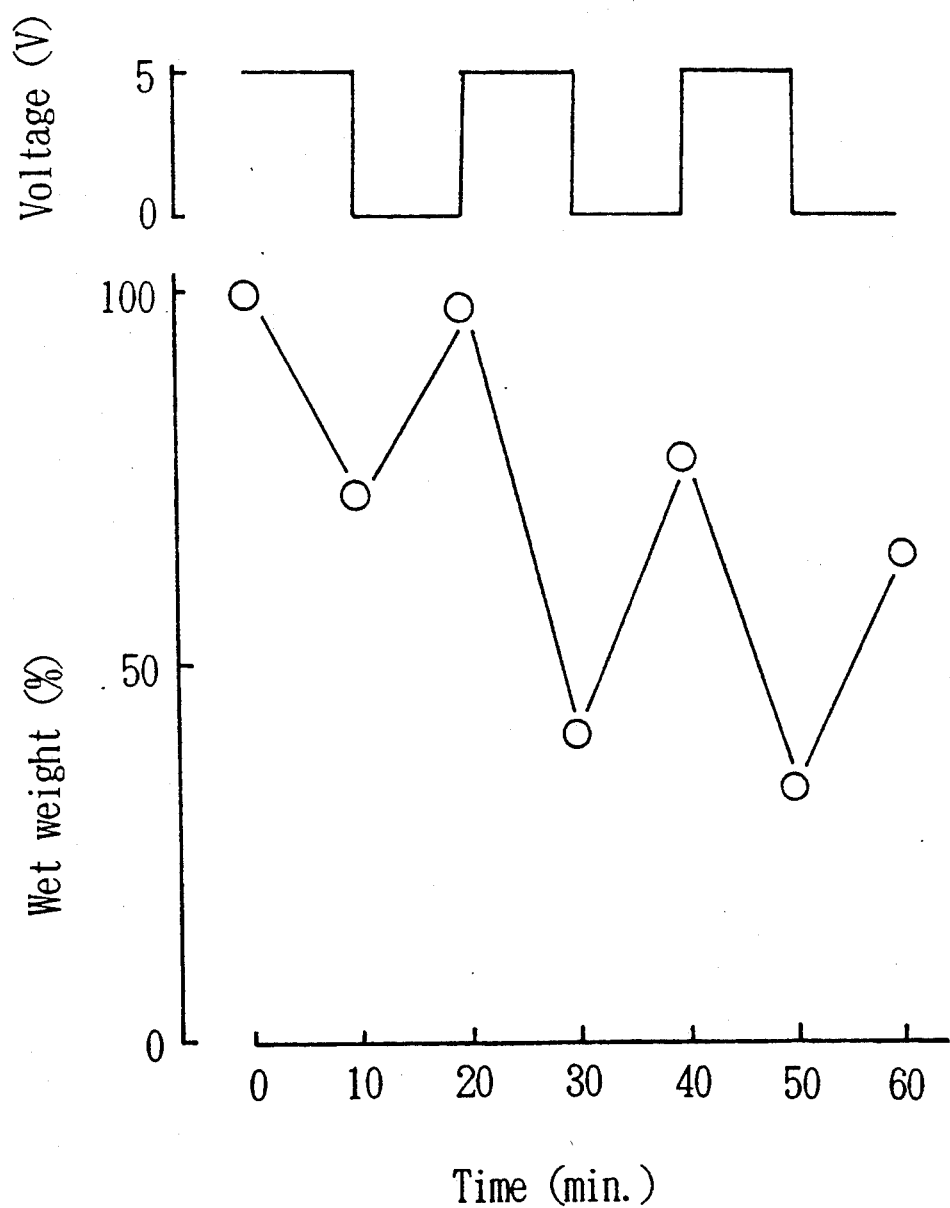
FIG. 1 shows contraction and reswelling of a hydrogel in response to voltage loading and unloading.

Any biosensor can serve for the present invention as long as it is capable of detecting the indicator chemical substance in vivo, with preference given to an ion sensitive field effect transistor (hereinafter referred to as ISFET) having an enzyme immobilized on its element. Such an ISFET is produced, for example, as follows: A photocuring resin mixed with a particular enzyme is coated on said element by dipping and immobilized thereon by near ultraviolet irradiation. The present inventors confirmed that a potential difference according to the indicator substance in solution can be produced by using such a biosensor.

In this case, any substance capable of reacting with said enzyme to produce a hydrogen ion can be used as an indicator chemical substance in vivo. Therefore, glucose can be used as an indicator when, for instance, a biosensor produced by immobilizing glucose oxidase is used.

The voltage produced by a biosensor thus prepared is normally of the order of millivolts (mV). On the other hand, the voltage necessary to contract the electroresponsive hydrogel described below is normally of the order of volts (V). Therefore, direct introduction of the voltage obtained using the biosensor into the hydrogel fails to cause efficient contracting of the hydrogel. In consideration of this fact, the present inventors placed an amplifier between the biosensor and the hydrogel, amplified the voltage obtained with the biosensor and introduced it into the hydrogel. The inventors thereby succeeded in efficient contracting of a hydrogel according to the output from a biosensor.

In this case, any amplifier can be used as long as it is capable of amplifying the voltage of the order of mV generated from the biosensor into a voltage of the order of V at a constant rate of about 1000 fold.

The hydrogel used for the present invention should be a hydrogel obtained by the alkali hydrolysis of a copolymer comprising N-isopropylacrylamide, an ionic monomer (preferably, an anionic monomer such as acrylic acid or methacrylic acid) and a crosslinking agent. In producing such a hydrogel, N-isopropylacrylamide and an ionic monomer are copolymerized in the presence of a crosslinking agent, and the resulting copolymer is hydrolyzed with alkali. In the reaction of N-isopropylacrylamide and an ionic monomer, it is preferable to carry out the reaction between 100 parts by weight of N-isopropylacrylamide and 5 to 50 parts by weight of an ionic monomer. Examples of the crosslinking agent to be present in the reaction system include ethylene glycol dimethacrylate, diethylene glycol dimethacrylate, triethylene glycol dimethacrylate and polyethylene glycol #200 dimethacrylate (produced by Shin Nakamura Kagaku Kogyo; number of ethylene units=4). It is preferable that these crosslinking agents be used in a ratio of 2 to 15 parts by weight to 100 parts by weight of the above-mentioned N-isopropylacrylamide. It is still more preferable that the hydrogel for the present invention be a hydrogel produced by hydrolyzing a copolymer comprising 100 parts by weight of N-isopropylacrylamide, 10 to 40 parts by weight of an anionic monomer described above and 5 to 10 parts by weight of a crosslinking agent described above.

In the performance of copolymerization, the above-mentioned components are each dissolved in dimethylsulfoxide (hereinafter referred to as DMSO) or distilled water, after which the reaction is initiated by the addition of a polymerization initiator or by the irradiation of ionizing radiation. Any type of ionizing radiation such as X ray, γ ray, β ray, α ray and electron beam can serve well, with particular preference given to γ ray. When using γ ray for copolymerization, it is ideal to irradiate the monomer mixture with 20 to 30 kGy of γ ray at room temperature in a nitrogen atmosphere.

When using a polymerization initiator for copolymerization, the reaction can be carried out using in combination ordinary polymerization initiators such as benzoyl peroxide and N,N-dimethyl-p-toluidine in an ordinary ratio in the presence of DMSO, or using in combination ordinary polymerization initiators such as ammonium persulfate and tetramethylethylenediamine in an ordinary ratio in the presence of distilled water.

Hydrolysis after completion of copolymerization can be carried out in an alkali. When using 1N NaOH or 1N KOH at room temperature to carry out the reaction, it is appropriate to carry out the reaction for 4 to 20 hours.

Into the hydrogel thus obtained, a physiologically active substance is incorporated. Any physiologically active substance can be incorporated into the hydrogel as long as the corresponding indicator substance is detectable by the biosensor. Examples of such physiologically active substances include insulin, antihyperlipidemic agents, antiallergic agents and antipsychotic drugs. The indicator substances corresponding to these physiologically active substances are detected using an ISFET having glucose oxidase, lipase, antigen/antibody, acetylcholine receptor, as respectively immobilized thereon, and the generated voltage is introduced into the hydrogel, whereby the physiologically active substance present in the hydrogel is released. In summary, when using ISFET as a biosensor, the indicator substance in vivo can easily be detected as a potential difference due to ions such as proton, sodium ion and potassium ion and positively or negatively charged polar substances, produced by the reaction of the substance immobilized on the sensor and the indicator substance. This mechanism makes it possible to release the physiologically active substance with appropriate timing.

In the present invention, incorporation of a physiologically active substance into the electroresponsive hydrogel can easily be achieved by immersing the hydrogel in a solution containing said physiologically active substance after hydrogel lyophilization, or can also be achieved by copolymerization after mixing the physiologically active substance in the monomer mixture constituting the hydrogel.

The hydrogel containing a physiologically active substance thus prepared is used as follows: The biosensor produced as above is brought into contact with an enzyme substrate indicator substance such as glucose in a solution; the resulting voltage is amplified with an amplifier and introduced into the hydrogen containing the physiologically active substance, whereby the hydrogel contracts and, in response thereto, the physiologically active substance incorporated in the hydrogel is released. Thus, release of the physiologically active substance can take place according to the concentration of the indicator chemical substance.

Since the hydrogel according to the present invention is capable of releasing a physiologically active substance alone in an amount corresponding to the applied voltage with excellent reproducibility by contracting and reswelling in good response to the loading and unloading of an external stimulation voltage, it can be advantageously used in a physiologically active substance release control system capable of releasing an essential physiologically active substance in a necessary amount according to changes in physiological conditions. Also, the physiologically active substance release control system of the present invention using this hydrogel is useful for the treatment of various diseases including diabetes mellitus since it is capable of controlling the release of insulin, for instance.

The hydrogel of the present invention can also serve well as artificial muscle, actuater for robots, switch, memory element, solvent pump, functional membrane, etc.

Since the hydrogel of the present invention is capable of sensing, for instance, blood sugar level, etc. by means of a minute biosensor, it can serve well in an artificial organ type control system capable of controlling the release of a physiologically active substance such as insulin according to changes in physiological conditions in vivo (e.g. changes in indicator substance concentration) which comprises at least a biosensor, an amplifier and an electroresponsive hydrogel containing a physiologically active substance and implanted in vivo.

EXAMPLE 1

Preparation of hydrogel

N-isopropylacrylamide (2.4 g), 0.45 g of acrylic acid and 0.15 g of diethylene glycol were dissolved in 4.8 ml of DMSO. This solution was packed in a glass ampule and irradiated with γ ray (25 kGy) generated from $^{60}$Co at room temperature in a nitrogen atmosphere to initiate polymerization. The resulting polymer was taken out from the ampule and immersed in deionized water. After removing the solvent and the unreacted portion of the monomer, the polymer was immersed in a 1N NaOH solution at room temperature for 18 hours to hydrolyze it, after which it was washed with water to yield a hydrogel.

Experiment 1-1

The hydrogel prepared above was inserted between platinum electrodes and applied with a voltage of 2 or 5 V/cm$^2$ in deionized water for a given period, and its weight was measured regularly to evaluate its electroresponsivity.

The hydrogel showed electroresponsivity in deionized water; it contracted quickly with time under voltage load. At 5 V/cm$^2$, it contracted to about 5% of the initial weight to reach an equlibrium in about 5 hours. The contracted hydrogel reswelled quickly in response to voltage unloading; it showed a recovery to about 83% its initial weight after about 48 hours.

Also, when voltage was applied for 2 hours, the hydrogel contracted to 46% of the initial weight at 2 V/cm$^2$ and to about 10% of the initial weight at 5 V/cm$^2$, and quick reswelling occured in response to voltage unloading in both cases. These results revealed that hydrogel contraction occured according to the intensity of the applied voltage.

Experiment 1-2

The hydrogel prepared above was inserted between platinum electrodes and applied with a voltage at 5 V/cm$^2$ in a 0.01M phosphate buffer, pH 7.4, for a given period, and its weight was measured regularly to evaluate its electroresponsivity.

As shown in FIG. 1, the hydrogel contracted quickly in response to voltage loading and reswelled quickly in response to voltage unloading in the phosphate buffer.

EXAMPLE 2

Preparation of hydrogel

The same monomer components in the same amounts as those in Example 1 were dissolved in 8.6 ml of water, followed by the similar procedure as in Example 1 to yield a hydrogel. This hydrogel showed an electroresponsivity equivalent to that of the hydrogel obtained in Example 1.

EXAMPLE 3

Preparation of insulin-containing hydrogel

Bovine insulin (produced by Sigma) was dissolved in a 0.01M phosphate buffer to reach a final concentration of 100 IU/ml, and pH was adjusted to 7.4. After lyophilization, the hydrogel prepared in Example 1 was immersed in the insulin solution described above and reswelled at 4° C. to yield an insulin-incorporated hydrogel.

Experiment 3-1

The insulin-containing hydrogel prepared above was inserted between platinum electrodes and applied with a voltage at 5 V/cm$^2$ in a 0.01M phosphate buffer for a given period, and the amount of insulin released was measured.

Figure 2:
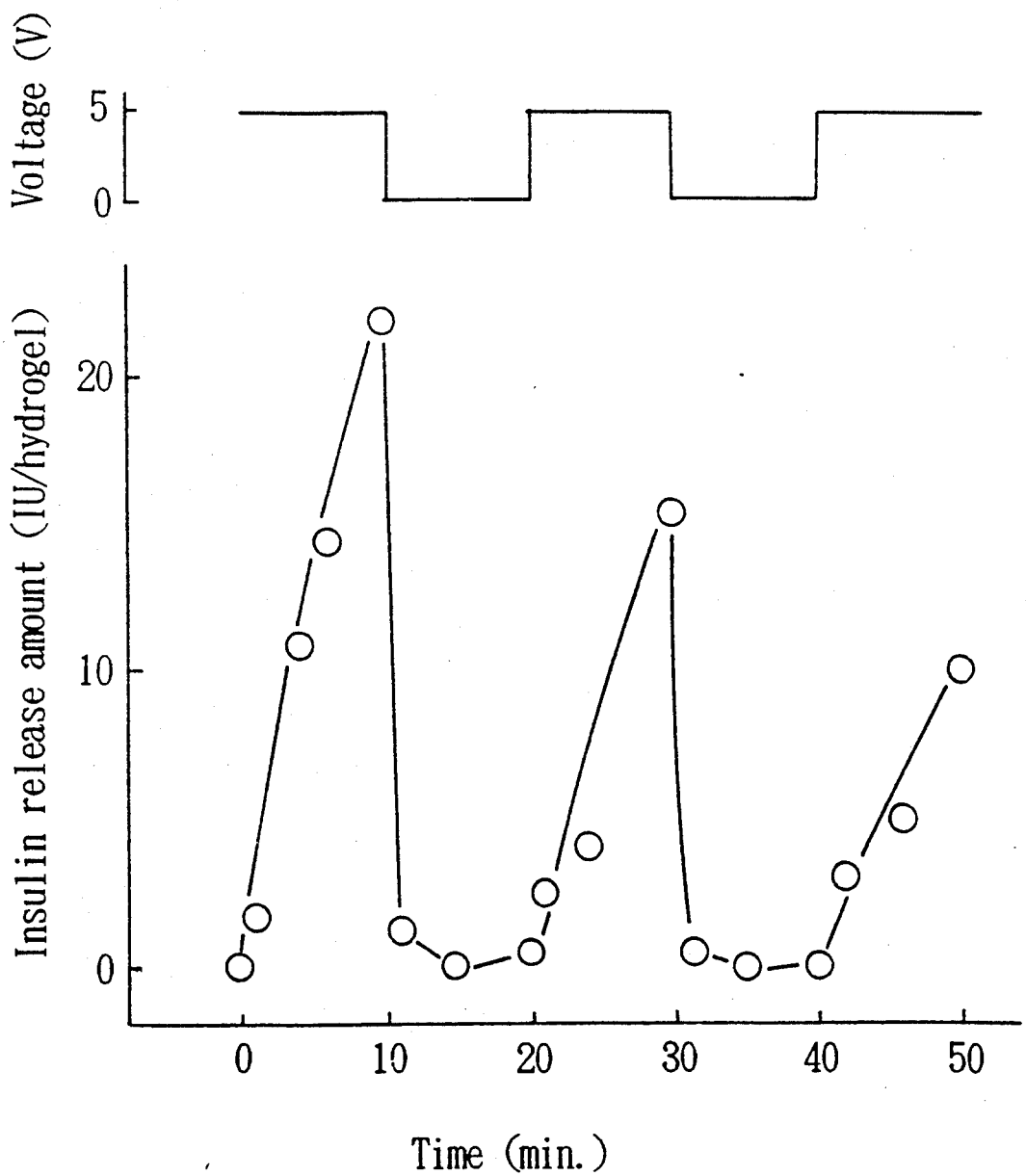
FIG. 2 shows a pattern of insulin release from an insulin-containing hydrogel in response to voltage loading and unloading.

As shown in FIG. 2, it was confirmed that insulin was released only when a voltage is applied to the hydrogel.

EXAMPLE 4

Physiologically active substance release control system

1. Biosensor

An ISFET element was immersed in a mixed solution (pH 7) of (3-aminopropyl)triethoxysilane and distilled water in a 1 to 10 ratio (50° C., 2 hours) to treat the element's surface. After the treatment, the element was washed with distilled water and dried.

A solution comprising 30 mg of glucose oxidase and 0.1 ml of distilled water was mixed with a solution of the following composition, followed by vigorous agitation.

Photosetting resin ENTV-500 0.2 ml
LSS-3380 (3-methacryloxypropyltrimethoxysilane):0.02 ml
Benzoin ethyl ether:0.004 ml The solution prepared above was coated (by dipping) on the surface of the surface-treated ISFET element described above and set by irradiation with light at a main wavelength of 366 nm from a black light fluorescent lamp for 3 minutes to yield a biosensor.

2. Insulin-containing hydrogel

An insulin-containing hydrogel as prepared in Example 3 was used.

3. Amplifier

A differential amplifier 5305 (produced by NF Kairo Sekkei Block) offering a maximum gain of 1000 against 50Ω load with a frequency band of DC 10 MHz and a maximum skewness of 0.02% was used at an amplification rate of 1000 fold.

4. Configuration of physiologically active substance release control system

Figure 3:
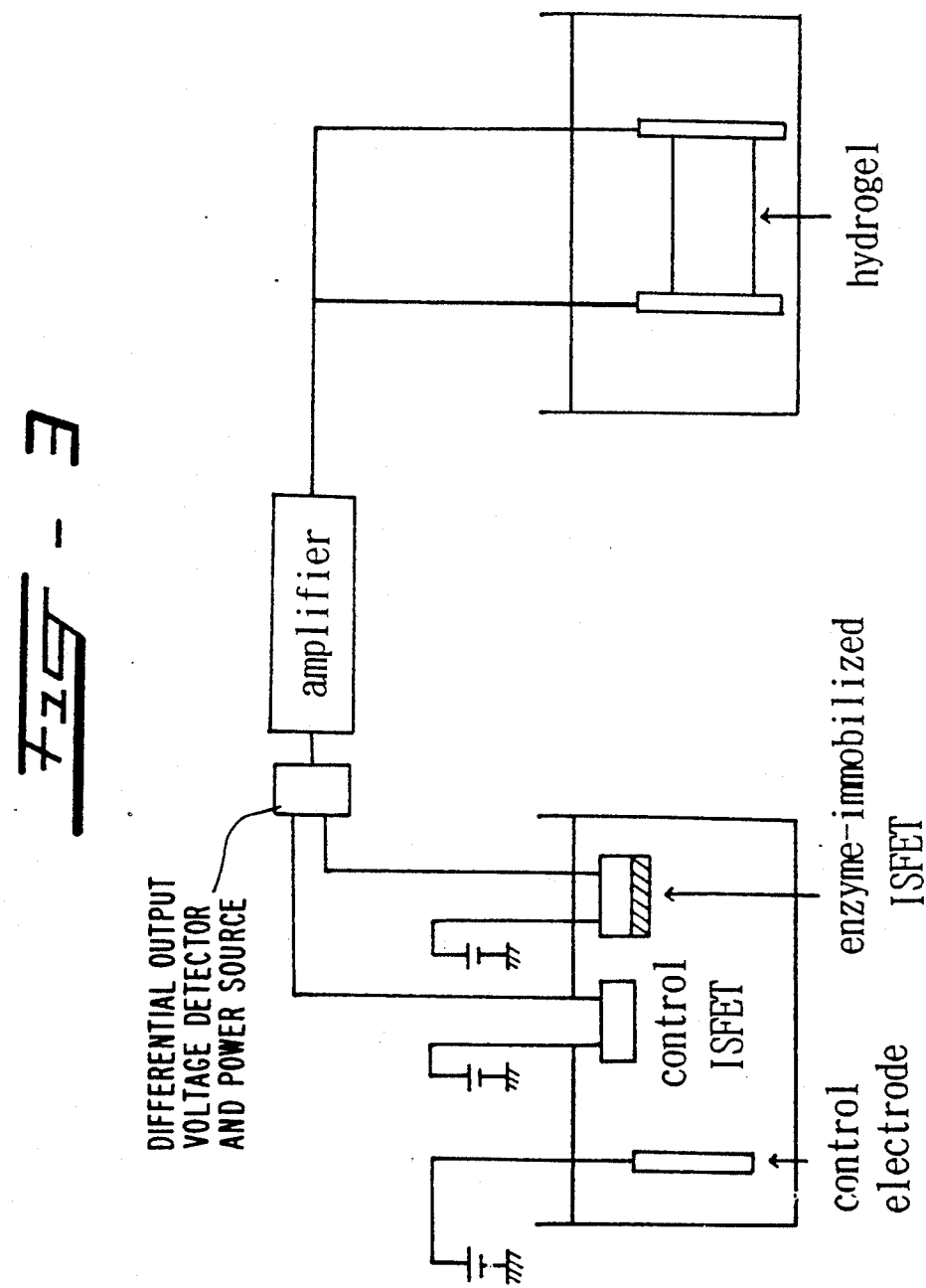
FIG. 3 shows the configuration of a physiologically active substance release control system.

The insulin-containing hydrogel, the biosensor and the amplifier described above were connected as illustrated in FIG. 3 to configure a physiologically active substance release control system. The hydrogel was inserted between platinum electrodes and immersed in a 0.01M phosphate buffer at pH 7.4. The biosensor was immersed in a 0.002M phosphate buffer at pH 5 containing 25 to 100 mg/dl glucose, and the amount of insulin released was measured for each glucose concentration. Also, as for the response of the system to repeated addition of glucose, it was rated by repeatedly adding after a given time 0.1 ml of 2.5% glucose (dissolved in a phosphate buffer) to 4.9 ml of a 0.01M phosphate buffer.

The insulin released from the hydrogel was assayed quantitatively by the HPLC method in accordance with the procedure of M. Ohta et al. [Chem. Pharm. Bull., 32, 4641 (1984)].

Figure 4:
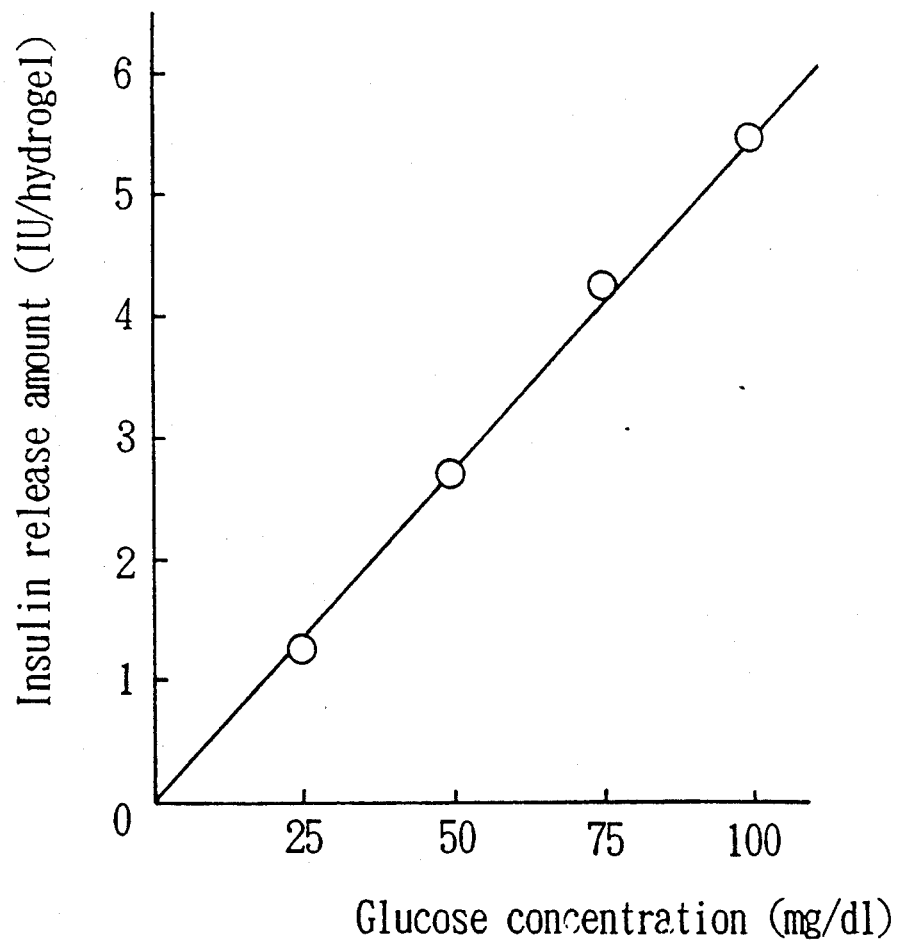
FIG. 4 shows the amount of insulin released from a hydrogel according to each concentration of glucose in contact with a biosensor.

FIG. 4 shows the amount of insulin released from hydrogel when the biosensor was immersed in a glucose solution at various concentrations. It was confirmed that insulin was released from hydrogel in an amount in proportion to the glucose concentration.

Figure 5:
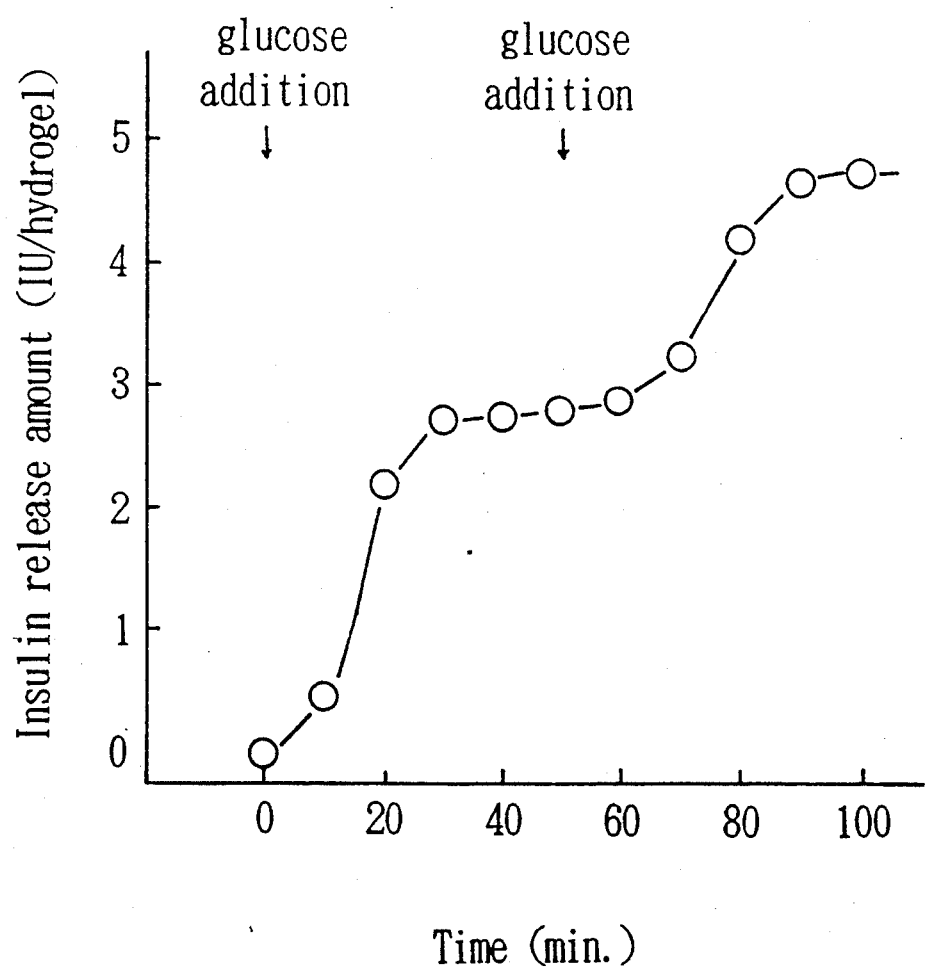
FIG. 5 shows a pattern of insulin release from a hydrogel obtained when glucose was added repeatedly to a biosensor.

FIG. 5 shows the results with repeated addition of glucose. Reproducible insulin release from hydrogel occurred in response to glucose addition to the biosensor side.

What is claimed is:

1. A physiologically active substance release control system which comprises:
   a biosensor for sensing the presence of an indicator chemical substance in vivo and for generating an electrical output voltage dependent upon the concentration of said indicator chemical substance in vivo,
   an amplifier for receiving said electrical output voltage and for amplifying said voltage and providing an output signal corresponding thereto, and
   an electroresponsive hydrogel containing a physiologically active substance for receiving said output signal from said amplifier and for contracting in response thereto, thereby releasing said physiologically active substance therefrom.

2. A physiologically active substance release control system as claimed in claim 1 wherein the biosensor is an ion sensitive field effect transistor having an enzyme immobilized on its element.

3. A physiologically active substance release control system as claimed in claim 2 wherein the indicator chemical substance is a substance capable of reacting with said enzyme to produce hydrogen ions.

4. A physiologically active substance release control system as claimed in claim 1 wherein the biosensor is produced by coating a photocuring resin mixed with a particular enzyme on said element by dipping and immobilizing it by near ultraviolet irradiation.

5. A physiologically active substance release control system as claimed in claim 1 wherein the amplifier is capable of amplifying the voltage from the biosensor at a constant rate of about 1000 fold.

6. A physiologically active substance release control system as claimed in claim 1 wherein the electroresponsive hydrogel is prepared by the alkali hydrolysis of a copolymer comprising N-isopropylacrylamide, an ionic monomer and a crosslinking agent.

7. A physiologically active substance release control system as claimed in claim 1 wherein the electroresponsive hydrogel is produced by hydrolyzing a copolymer comprising 100 parts by weight of N-isopropylacrylamide, 5 to 50 parts by weight of an ionic monomer and 2 to 15 parts by weight of a crosslinking agent.

8. A physiologically active substance release control system as claimed in claim 1 wherein the electroresponsive hydrogel is produced by hydrolyzing a copolymer comprising 100 parts by weight of N-isopropylacrylamide, 10 to 40 parts by weight of an ionic monomer and 5 to 10 parts by weight of a crosslinking agent.

9. A physiologically active substance release control system as claimed in claim 1 wherein the physiologically active substance is insulin.

* * * * *